(12) United States Patent
Enos

(10) Patent No.: US 7,238,023 B1
(45) Date of Patent: Jul. 3, 2007

(54) SALIVA EJECTOR OR EDUCTOR

(76) Inventor: Denise A. Enos, 1066 Valley Butte Dr., Eugene, OR (US) 97401

( * ) Notice: Subject to any disclaimer, the term of this patent is extended or adjusted under 35 U.S.C. 154(b) by 82 days.

(21) Appl. No.: 11/012,379

(22) Filed: Dec. 14, 2004

(51) Int. Cl.
*A61C 17/06* (2006.01)

(52) U.S. Cl. .......................... 433/91; 433/96

(58) Field of Classification Search ............ 433/91–92, 433/94–96; D24/10; 604/35, 902
See application file for complete search history.

(56) References Cited

U.S. PATENT DOCUMENTS

| | | | |
|---|---|---|---|
| 2,595,666 A | | 5/1952 | Hutson |
| 2,637,106 A | | 5/1953 | Otis |
| 3,029,513 A | * | 4/1962 | Fletcher ...................... 433/94 |
| 3,090,122 A | * | 5/1963 | Erickson ...................... 433/93 |
| 3,541,583 A | | 11/1970 | Deuschle |
| 3,758,950 A | | 9/1973 | Krouzian |
| 4,058,896 A | * | 11/1977 | Moore .......................... 433/91 |
| 4,265,621 A | * | 5/1981 | McVey ......................... 433/91 |
| 4,904,238 A | * | 2/1990 | Williams ....................... 604/43 |
| D312,872 S | * | 12/1990 | Mahl ........................... D24/112 |
| 5,066,228 A | * | 11/1991 | Doundoulakis et al. ........ 433/91 |
| 5,114,342 A | | 5/1992 | Young et al. |
| 5,876,201 A | * | 3/1999 | Wilson et al. ................. 433/80 |
| 6,068,477 A | * | 5/2000 | Mahlmann .................... 433/96 |
| 6,299,444 B1 | * | 10/2001 | Cohen ........................... 433/91 |
| 2002/0161358 A1 | * | 10/2002 | Liu et al. ....................... 606/15 |
| 2003/0017433 A1 | * | 1/2003 | Reiz ............................. 433/93 |

* cited by examiner

*Primary Examiner*—Cary E. O'Connor
(74) *Attorney, Agent, or Firm*—Robert E. Howard

(57) ABSTRACT

A saliva ejector or eductor including an ejector tube having a suction end and a discharge end. The ejector tube has a wire embedded in the wall thereof adapted to allow the tube to be easily bent into a selected configuration and to retain that configuration. A hollow tip is secured to the suction end of the ejector tube. The tip has an upper face and a lower face. A plurality of tear-shaped openings extend solely through the upper face and communicate the interior of the tip with the exterior thereof.

9 Claims, 1 Drawing Sheet

SALIVA EJECTOR OR EDUCTOR

BACKGROUND OF THE INVENTION

The present invention relates to an improved saliva ejector or eductor.

Saliva ejectors are used during dental procedures to remove saliva and small particles, such as plaque, cleaning material, and ground away existing fillings and decayed tooth material. Such saliva ejectors include an ejector tube having a distal (upper) suction end and a proximal (lower) discharge end. The ejector tube typically has a metal wire embedded in the wall thereof to allow the tube to be bent to a desired angle and held in place, as shown, for example, in U.S. Pat. No. 3,541,583. The discharge end of the ejector tube is connected via a hose and hose valve to a vacuum source. The suction end of the ejector tube is fitted with a hollow tip having openings therein. The tip on the suction end of the ejector tube is inserted into a patient's mouth.

The ejector tube and tip are typically made of polyvinyl chloride or polyethylene. Such tips are hard and can irritate the tissue of a patient's mouth.

The tip typically has openings (slots) around its entire periphery. The suction force draws material into these openings and down the tube. If the tip contacts the patient's mouth tissue, it can suck the tissue into contact with the tip which is uncomfortable and can cause damage to the patient's mouth. Such prior art ejectors can require constant manual adjustments while in use and cause unpleasant sensations, bruising and anxiety to patients.

SUMMARY OF THE INVENTION

It is an object of the present invention to provide a saliva ejector which overcomes the aforementioned difficulties with existing saliva ejectors.

It is a further object to provide a device which can be used as an eductor in the fields of medicine and surgery for the removal of body fluids.

The saliva ejector of the present invention includes an ejector tube having a suction end and a discharge end. The ejector tube has a wire embedded in the wall thereof and is adapted to allow the tube to be easily bent into a selected configuration and to retain that configuration.

A hollow tip formed of a soft material is secured to the suction end of the ejector tube, the tip having a plurality of tear-shaped openings communicating the interior thereof with the ejector tube. The openings are located solely in the outer face of the tip to provide a suction area, the remainder of the tip being suction-free. The non-suction side is smooth and allows retraction on the non working side without trauma to fragile tissue.

DESCRIPTION OF PREFERRED EMBODIMENTS

Figure 1:
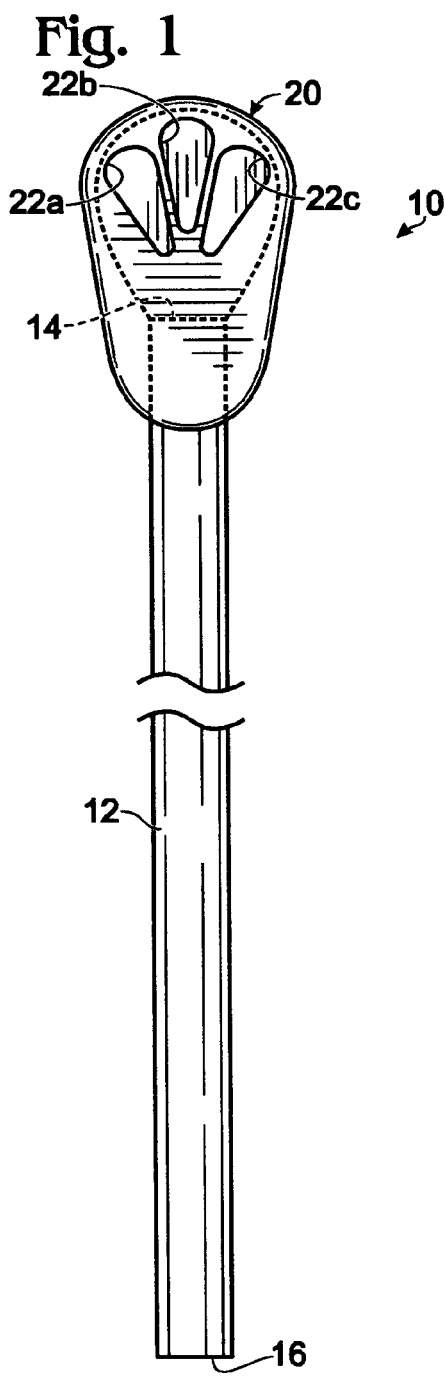
FIG. 1 is a top plan view of the saliva ejector of the present invention.
Figure 2:
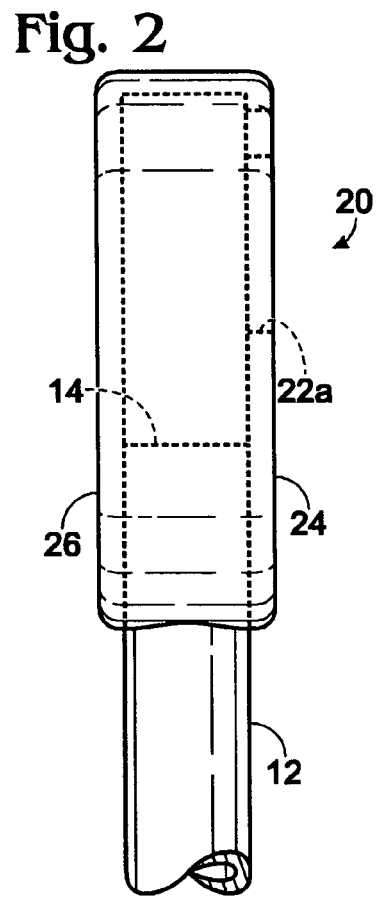
FIG. 2 is a left side elevational view of the improved tip of the saliva ejector of the present invention.
Figure 3:
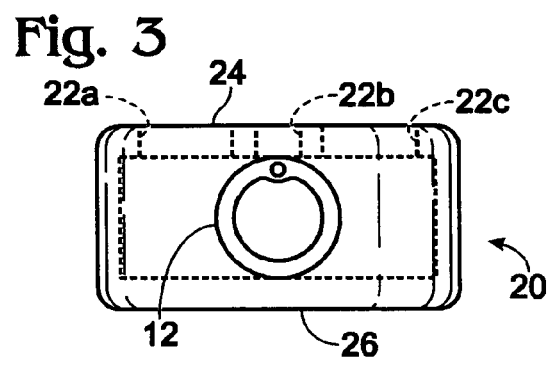
FIG. 3 is an elevational view of the proximal end of the improved tip of the saliva ejector of the present invention.

The saliva ejector 10 of the present invention includes an ejector tube 12 and a tip 20.

Ejector tube 12 has a suction end 14 and a discharge end 16, and is made of any suitable polymeric tubing, such as polyvinyl chloride or polyethylene. A wire (not shown) is embedded in the wall of ejector tube 12 in a manner well known in the art. The inside and outside diameters of ejector tube 12 are preferably substantially the same as that used with currently existing saliva ejector tubing.

The diameter of the wire embedded within the wall of ejector tube 12 is preferably slightly larger than that currently used in order to provide improved retention of shape when the tubing is bent. Current ejector tubes have an imbedded wire 0.032 inch in diameter (20 gage). The ejector tube of the present invention preferably has a larger diameter wire embedded therein, and preferably a diameter of about 0.064 inch (14 gage).

Tip 20 is hollow and has a pear shape, and is attached to the suction end of ejector tube 12 by any suitable means, such as a pressure fit, use of an adhesive, welding, or molding the ejector tube 12 and tip 20 as a single piece. A plurality of tear-shaped openings 22a, 22b, and 22c communicate the interior of tip 20 with the exterior thereof. Openings 22 only appear in outer face 24 of tip 20 to form a suction area, the inner face 26 and peripheral edges of the tip having no openings and are suction free during use.

Tear-shaped openings 22 each extend from adjacent the distal end of tip 20 to a location adjacent the mid-portion of the outer face 24 of tip 20. Preferably, three such tear-shaped openings 22 are present, with middle opening 22b being located along the longitudinal axis of the outer face 24, and with right and left openings 22a and 22c being positioned along the right and left sides of middle opening 22b, respectively.

By having openings 22 tear-shaped a higher uptake of aerosols generated during dental cleaning is achieved by virtue of larger particles passing into the larger portion of the opening and smaller particles passing into the smaller portion.

Tip 20 can be color coded, such as by having the outer face 24 containing openings 22 one color, and the remainder of the tip another color. Such color coding provides a quick check about the location of openings 22 to the user.

Tip 20 is made of a soft polymeric or synthetic rubber material, such as, for example, a silicon rubber of the type used to make earphones, or the soft polymeric material used to make BIOPLAST® orthodontic mouth guards sold by Scheu-Dental.

In use, ejector tube 12 is bent into the shape required function as a retractor and to suction saliva from a patient's mouth, with the outer face 24 of tip 20 containing openings 22 facing outwardly away from the patient's mouth tissue. The inner face 26 and peripheral edges of the tip 20 may come into contact with the mouth tissue of the patient during use; however, since there are no openings therein, there is no danger of the tissue being grabbed by the tip.

Although the device 10 has been primarily described for use as a saliva ejector, it can be used as an eductor in medical or surgical procedures to remove body fluids.

It will be obvious to those having skill in the art that many changes may be made to the details of the above-described embodiments of this invention without departing from the underlying principles thereof. The scope of the present invention should, therefore, be determined only by the following claims.

The invention claimed is:

1. A saliva ejector or eductor comprising:
    an ejector tube having a suction end and a discharge end, said tube having a wire embedded in the wall thereof and adapted to allow said tube to be easily bent into a selected configuration and to retain said configuration;

a hollow tip secured to the suction end of said ejector tube, said tip having an outer face having a longitudinal center line, an inner face, and distal and proximal ends, a plurality of tear shaped openings having distal and proximal ends, said openings being located solely in said outer face of said hollow tip, said distal end of each of said openings being located adjacent the distal end of said hollow tip, and the proximal ends of each of said openings being located adjacent the mid-portion thereof, the distal ends of each of said openings has a width greater than the width of the proximal ends of each of said openings, said openings communicating the interior of said hollow tip with the exterior thereof, said tip being made of a soft polymeric or synthetic rubber material.

2. The saliva ejector of claim 1 wherein there are three said openings.

3. The saliva ejector of claim 2 wherein a first opening is located along the longitudinal center line of said outer face, and the other openings are positioned on either side of said first opening.

4. The saliva ejector of claim 1 wherein said outer face of said tip containing said openings has a color different than the color of the remainder of said tip.

5. The saliva ejector of claim 1 wherein said wire has a diameter greater than 0.032 inch but not so great as to not allow a user to readily bend said ejector tube.

6. The saliva ejector of claim 5 wherein said wire has a diameter of up to about 0.064 inch.

7. The saliva ejector of claim 5 wherein said wire has a diameter of about 0.064 inch.

8. The saliva ejector of claim 1 wherein said hollow tip has a pear shape.

9. The saliva ejector of claim 8 wherein said distal end of said hollow tip is larger than said proximal end.

* * * * *